United States Patent [19]
Vijg et al.

[11] Patent Number: 5,470,706
[45] Date of Patent: Nov. 28, 1995

[54] PROCESS FOR THE RESCUE OF DNA AND FOR DETECTING MUTATIONS IN MARKER GENES

[75] Inventors: Jan Vijg, Rotterdam; Jan A. Gossen, Waddinxveen, both of Netherlands

[73] Assignee: Nederlandse Organisatie voor toegepastwetenschappelijk onderzoek TNO, The Hague, Netherlands

[21] Appl. No.: 13,198

[22] Filed: Jan. 29, 1993

Related U.S. Application Data

[63] Continuation of Ser. No. 382,242, Jul. 19, 1989, abandoned.

[30] Foreign Application Priority Data

Jul. 19, 1988 [NL] Netherlands ............................ 8801826

[51] Int. Cl.⁶ ............................................................. C12Q 1/68
[52] U.S. Cl. ......................... 435/6; 435/91.2; 435/172.1; 435/172.3; 435/243; 435/244; 536/22.1; 536/23.1; 935/19; 935/23; 935/29; 935/56; 935/57; 935/83; 935/84
[58] Field of Search ........................... 435/6, 91.2, 172.1, 435/172.3, 243, 244; 536/22.1, 23.1; 935/19, 23, 29, 56, 57, 83, 84

[56] References Cited

U.S. PATENT DOCUMENTS

| 4,753,874 | 6/1988 | Calos | 435/6 |
|---|---|---|---|
| 5,347,075 | 9/1994 | Sorge | 800/2 |

FOREIGN PATENT DOCUMENTS 0289121  11/1988  European Pat. Off. .

OTHER PUBLICATIONS

Kohler et al. (1990) Nucleic Acids Research, vol. 18, No. 10, pp. 3007–3013.
Raleigh et al. (1986) Proc. Nat'l Acad Sci (USA), vol. 83, pp. 9070–9074.
Stratagene Cloning Systems Catalog (1988), La Jolla, Calif.
Maniatis et al. (1982) *Molecular Cloning, A Laboratory Manual* (Cold Spring Harbor Lab., N.Y.) pp. 11–27 and 504–506.
Glazer et al. (1986) Proc. Natl Acad Sci (USA) vol. 83, pp. 1041–1044.
Mechanisms Of Ageing And Development, J. Vijg et al., "A search for DNA alterations in the aging mammalian genome: an experimental strategy", vol. 41, 1987, pp. 47–63.
Nucleic Acids Research, J. Gossen et al., "*E. coli* C: a (List continued on next page.)

*Primary Examiner*—W. Gary Jones
*Assistant Examiner*—Ardin H. Marschel
*Attorney, Agent, or Firm*—Webb Ziesenheim Bruening Logsdon Orkin & Hanson

[57] ABSTRACT

The invention relates to a process for the rescue and cloning of a DNA sequence wherein a vector containing said DNA sequence is multiplied in a suitable bacterial host. As the bacterial host, a bacterial strain which is incapable of host restriction is used, such as an *Escherichia coli* C strain. Preferably, a bacteriophage vector which is a suitable cloning vehicle for the bacterial host concerned is used as the vector, the step of in vitro packaging into phage coats being performed by means of a phage packaging extract obtained from a bacterial strain which is incapable of host restriction. The invention may be used in a process for detecting mutations in one or more marker genes introduced into a mammalian genome by means of a vector, which process comprises isolating DNA from cells of the transgenic mammal or from the mammalian cells, recovering the vector from said DNA, multiplying the vector in a suitable bacterial host which is deficient with respect to at least one of the marker genes, and testing marker gene expression. Preferably, the DNA isolated from cells of the transgenic mammal or the mammalian cells is pre-purified by fragmenting the DNA by means of a restriction enzyme which does not have a cutting site within the vector, separating the resulting fragments on the basis of a suitable criterion, such as differences in size, and collecting fragments comprising the vector, whereafter the vector is recovered from said pre-purified DNA.

20 Claims, 5 Drawing Sheets

OTHER PUBLICATIONS convenient host strain for rescue of highly methylated DNA", Oct. 11, 1988, p. 9343.

Chemical Abstracts, V. M. Kramarov et al., "Recombinant plasmid pBP5RM and method for constructing it and *Escherichia coli* strain C 600 P5 RM—a producer of site–specific endonuclease V and II", vol. 107, 1987, abstract No. 110455n; and Otkrytiya, Izobret 1987, (9), 110, abstract.

Methods In Enzymology, J. Collins, "*Escherichia coli* plasmids packageable in vitro in a bacteriophage particles", 1979, vol. 68, pp. 309–626.

Mutation Research, P. H. M. Lohman et al. "DNA methods for detecting and analyzing mutations in vivo", 1987, vol. 181, pp. 227–234.

Nucleic Acids Research, E. A. Raleigh et al., "McrA and McrB restriction phenotypes of some *E. coli* strains and implications for gene cloning", 25 Feb. 1988, vol. 16, No. 4, pp. 1563–1575.

W. B. Wood, "Host Specificity of DNA produced by *Escherichia coli*: Bacterial Mutations affecting the Restriction and Modification of DNA," J. Mol. Bio., 16, 118–133 (1966).

PROCESS FOR THE RESCUE OF DNA AND FOR DETECTING MUTATIONS IN MARKER GENES

This is a continuation of copending application Ser. No. 07/382,242 filed on Jul. 19, 1989, now abandoned.

This invention relates to a process for the efficient rescue and cloning of DNA sequences from genomes in general, in particular methylated DNA sequences, and relates more specifically to a process for detecting mutations in one or more marker genes introduced into a mammalian genome by means of a vector, which process comprises isolating DNA from cells of the transgenic mammal or from the mammalian cells, recovering the vector from said DNA, multiplying the vector in a suitable bacterial host deficient with respect to at least one of the marker genes, and testing the expression of the marker gene.

Such a process is known from the articles by Lohman et al. 1987; and Vijg and Uitterlinden, 1987, disclosing an animal test model, inter alia for estimating the risks of potentially carcinogenic agents. More in particular, they propose a mouse model for in vivo mutation analysis using transgenic mice of which all cells, including the germ cells, comprise a bacteriophage lambda vector integrated in the genome, which vector is provided with a selectable marker. Testing of agents for carcinogenicity is of great importance in a society in which more and more newly synthesized agents make their appearance. Many of these agents, as well as a number of already existing chemical compounds are suspected of carcinogenicity. According to present day insights cancer would be based on changes in the DNA base sequence of certain genes. Mutagenic agents (i.e. agents that change the base sequence of the DNA) are nearly always carcinogenic and can also cause permanent damage to the heritable material (and therefore lead to hereditary diseases). Consequently, the ability of an agent to introduce mutations into genes is considered to be an important criterion for estimating the risks of the relevant agent as regards injurious effects on health, such as cancer and deviations in the hereditary information.

The best known test for potentially mutagenic agents is the Ames test dealing with mutations in bacteria (Ames et al., 1973). Probably, because bacteria are rather remote from man, this test is not 100% reliable (Zeiger et al., 1987). For this reason preference is often given to a combination of tests, including tests with mouse cells. As applies to all mammalian cells, the genome of mouse cells is too complicated for mutation studies analogous to the Ames test; a great advantage of bacteria is that they have very short generation times, which enable selection for certain mutations, as well as their characterization.

An important problem with cultured mammalian cells as a model in mutagenicity tests is the artificial aspect of the in vitro situation and the impossibility to test for differences between organs and tissues as regards nature and frequency of induced mutations. For instance, it may be very important to know whether a certain agent preferably induces mutations in the germ cells, or just the reverse. On the other hand, information is necessary with respect to the possibility of drawing conclusions on mutations in certain organs on the basis of measurements on blood cells. This is important, for instance, when screening people who may have been exposed to dangerously high doses of a carcinogenic agent.

At this moment there are only few possibilities of testing mutations in vivo in cells of higher animals. An example is the so-called HPRT test in which mutations in the HPRT gene are selected on the basis of the 6-thioguanine resistance of the isolated and cultured cells (Albertini et al., 1982). This method is labour-intensive and only allows measurements on cells that can still divide and are easy to culture. In addition the HPRT method is prone to artefacts (Featherstone et al., 1987).

The approach suggested in the above-mentioned articles by Lohman et al., 1987 and Vijg and Uitterlinden, 1987, implies that a bacteriophage lambda vector integrated in the mouse DNA, which vector contains one or more selectable bacterial genes, can be recovered from total chromosomal DNA by mixing this DNA with an enzyme cocktail which cuts the vector at the flanking "cos sites" from the mouse DNA and then encapsulates it. Subsequently, the packaged phages together with an excess of bacteria are plated on a nutrient medium, which after a few hours results in a number of so-called plaques, i.e. circular clear areas in the bacterial lawn. Each plaque corresponds to one recovered vector. If the marker gene in the phage is intact, it will be expressed. The absence of expression is therefore indicative of a mutation in the marker gene.

For completeness' sake, it should be mentioned here that the above approach cannot be adopted with naturally present genes. These simply cannot be isolated from the DNA of an organ with great efficiency, in contrast to the integrated vector, which has special properties including the presence of two half cos sites at both sides of the vector. If the vector is integrated in the mouse DNA in a head-to-tail arrangement, the central vectors can be cut from the mouse DNA at the whole cos sites. It is therefore essential, at least with vectors flanked by half cos sites, that at least 3 vectors integrate in a head-to-tail arrangement. In the case of vectors flanked by whole cos sites this is not necessary.

An example of a marker gene is the bacterial gene lacZ. With this (and with other corresponding marker genes) frequency and nature of mutations in cells or in the different organs and tissues of a transgenic animal can be simply determined by means of the above described recovery of the vector and its transfer to bacteria. The lacZ gene codes for β-galactosidase which converts X-gal (the substrate) to a blue substance. X-gal can be added to the nutrient medium on which the bacteriophages are plated with an excess of bacteria. Each phage will give rise to a blue plaque if the lacZ gene is still intact. Mutations in this gene reveal themselves by leaving the plaques uncoloured as a result of the inactivation of the lacZ gene. Each uncoloured plaque is a small reservoir of mutated genes which can be easily analyzed further if this is deemed necessary. There are a number of different mutation target genes (lacZ, lacI, lacZα, supF, cI, galK, LacO, gpt, etc.), a number of which can be incorporated into a vector simultaneously or separately.

The above described system can only operate if the vector can be recovered with a sufficiently high degree of efficiency. In theory, one would like to "rescue" a vector from each cell of a certain organ in order to establish whether a mutation has occurred therein. In practice, one can be satisfied with about 100,000 vectors from a certain organ. For on the basis of the above described HPRT tests (in white blood cells) the assumption is that the spontaneous mutation frequency is at most about 1 to 100,000 (Albertini et al., 1985), i.e. out of 100,000 cells in normal adult individuals, on the average about one or less will be inactivated for each gene by a mutation at a certain site. This applies to protein-coding, naturally present genes.

Up to now, there are no indications that bacteriophage lambda vectors (or other integrated vectors) can be recovered in more than a few tens per μg genomic DNA (Lindenmaier et al., 1982; Glazer et al., 1986). A very large amount of phage packaging extract (the enzyme cocktail) is necessary to rescue the integrated vectors from more than a few micrograms of genomic DNA. In view of the high price of the present commercially sold phage packaging extracts a simple scale-up of the procedure for the purpose of recovering more vectors is not practical. The low phage packaging efficiency may be the reason that up to now the above described system has not been used as a mutation model, neither in the form of cell lines nor in the form of transgenic mice. It is true that extensive use is made of vectors having mutation target genes thereon, but always without allowing them to integrate (see for a survey Lehmann, 1985 and Dubridge and Calos, 1988). An exception is the work by Glazer et al. (1986), according to which a bacteriophage lambda vector provided with a bacterial mutation target gene was brought into a cell line by means of transfection. The integrated gene was then recovered and analyzed for mutations. The efficiency of the recovery, however, was low.

Recently, the present inventor and colleagues have succeeded in making transgenic mice with in each cell one or more copies of a bacteriophage lambda vector provided with a lacZ mutation target gene. In the animals with at least 3 or more tandem integrated vectors, in vitro packaging into phage particles from total genomic mouse DNA is possible in principle. In the first instance, however, it turned out again that the vector could not be recovered with a fair degree of efficiency.

The present invention provides a solution to this problem and thereby provides a method for the efficient rescue and cloning of methylated DNA in general, and more specifically for the efficient rescue of integrated vectors from total chromosomal DNA of different organs and tissues of a transgenic mammal or from total chromosomal DNA of a cultured mammalian cell line (in particular, this is to be taken to mean a cell line obtained by transfection with the vector, or more in particular, any mammalian cell line containing the vector, irrespective of how the cell line has been obtained).

The invention is based on the insight resulting from further research that the integrated vectors were completely methylated with all tested mice. In other words, in the organs and tissues of the tested transgenic mouse strains all tested cytosine residues in the vector were found to be provided with a covalently bound 5-methyl group. It is known that certain forms of methylation render bacteria capable of so-called host restriction (Raleigh et al., 1986). That is to say, entering DNAs (such as, for instance, the bacteriophage lambda vectors) are cut into pieces by way of defence before they get the chance of controlling and finally killing their host (which gives rise to lytic plaques). It was conceived that this phenomenon might be accountable for the low number of plaques obtained in practice. Because the conventional, commercially sold phage packaging extracts are made from bacteria and bacteria are also necessary to plate the phages (as a host), it was decided for both purposes to work only with bacterial strains which are incapable of host restriction. To this end, the phage packaging extracts could be obtained from Stratagene (Stratagene Cloning Systems, 11099 North Torrey Pines Road, LaJolla, Calif. 92037 USA), which in contrast to other firms supplies phage packaging extracts that according to our experiments probably originate from *E. coli* C, a strain incapable of host restriction. The latter has never been explicitly mentioned by this firm in their brochures or in their manuals. For plating, however, the firm does not supply a host restriction-negative strain, such as *E. coli* C, together with the extracts, but other strains which happen to be capable of host restriction. The necessity to use a packaging extract derived from a host restriction-negative *E. coli* strain in combination with the same, or a comparable, host restriction-negative strain for plating, has never been reported to be necessary for the rescue of methylated DNA. This is illustrated by the present lack of cloning systems for methylated mammalian DNA. The *E. coli* C strain, used in the studies that gave rise to this invention, is known per se and, for instance, obtainable from the Phabagen collection (University of Utrecht, Department of Molecular Cell Biology, Padualaan 8, P.O. Box 80.056, 3508 TB Utrecht). By means of gamma radiation variants were then obtained which lacked the entire lacZ gene. This was necessary for the purposes of the experiments described herein, because otherwise selection for inactivation of lacZ in the vectors to be packaged was not possible.

Using the obtained *E. coli* C lacZ$^-$ strain, about 9,000 vectors were recovered from about 1 µg total genomic DNA of one transgenic mouse strain. The blue colour of the plaques suggested that in all these cases the lacZ gene was not mutated.

This phage packaging efficiency is by far the highest ever obtained from total chromosomal DNA and is in principle sufficient for research into induced mutations.

While the essence of the invention resides in the use of bacterial strains incapable of host restriction, such as preferably *E. coli* C strains, it has further been found conducive to a high phage packaging frequency that a large number of copies of the vector is integrated in the mammalian genome in a head-to-tail arrangement. In the transgenic mouse strain (20.2) which enabled the above result, this copy number proved to be about 80. This means that the genome of the mice in question contains some additional 4 millions of base pairs of DNA. Also with other strains the vector proved to be integrated in a large number of copies. For instance, strain 40.6 has the vector in about 40 copies. The stable inheritance of so much additional DNA has not been reported before.

However, in order to obtain a reliable picture of the mutation frequency in different organs and tissues at low doses of the suspected agent, it is necessary to test much more than 9,000 plaques. As stated above, a scale-up of the phage packaging reaction by using more genomic DNA is expensive. Take the case, for instance, that a suspected agent increases the mutation frequency from 1 : 100,000 (spontaneous frequency) to 1 : 50,000. In theory, on the basis of the efficiency obtained one would have to carry out a phage packaging experiment with 5 µg total genomic mouse DNA. From this one would get one mutant (one uncoloured plaque). It will be clear that this is not sufficient in practice; for a close determination of such a low mutation frequency at least 500,000 to 1 million of plaques will have to be viewed.

According to a preferred embodiment of the invention this problem was solved by carrying out a pre-purification based on the idea that if the vectors could be separated from the rest of the chromosomal DNA, the ratio of the vector to the rest of the genome becomes much more favourable. This means that many more vectors can be recovered with the same amount of phage packaging extract. But the question was how to separate the integrated vectors from the rest of the chromosomal DNA.

It was thought that if the vector, which is about 50,000 base pairs long, has no recognition sites for a certain restriction enzyme which frequently cuts in total genomic mammalian DNA, this gives a fragment of about 1.5 millions of base pairs after tandem integration in, e.g., 30 copies. Since a restriction enzyme frequently cutting in mammalian DNA generates fragments having an average size of about 5000 base pairs, such a large fragment can be rapidly purified by means of a simple separation method.

The vector used by the inventor and colleagues contained no recognition sites for the enzyme XbaI. It has turned out that in a number of the available transgenic mice the vectors were integrated head-to-tail in 40–80 copies. Indeed, after cutting with XbaI a fragment of more than 1 million of base pairs proved to be easily separable from the rest of the (fragmented) genomic DNA. It was thought that a similar principle could also be used the other way round. Plasmids integrated in the genome (which are not larger than, e.g., about 5000 base pairs) can be simply rescued from total genomic DNA, provided they are flanked by restriction enzyme recognition sites unique for the plasmid; if rare restriction enzyme recognition sites (e.g., Not I) are applied to the left and right of the vector, a pre-purification is possible also here on the basis, in the present case, of precisely the small size of the plasmid-containing DNA fragment.

An alternative for pre-purification of the vectors is to interbreed the different mouse strains, each harbouring a vector-cluster at a different site in their genome. The latter was not checked, but integration of injected DNA in the mouse genome is random and it is therefore highly unlikely that two different transgenic mice are obtained with the vector-cluster at the same site on the same chromosome. The interbreeding will result in a mouse strain with multiple vector clusters at different sites in the genome. In such a "multi-locus" strain many more vectors can be rescued from each mouse cell and therefore the rescue frequency becomes much higher; the efficiency of rescue, which is entirely dependent on the use of host restriction-negative *E. coli* strains, such as *E. coli* C, does not change in this way.

Phage packaging experiments with pre-purified vector-containing genomic DNA of both untreated and ENU-treated transgenic mice (strain 20.2) showed that per DNA sample (about 100 µg total chromosomal mouse DNA) about 1,400,000 plaques could be obtained in one experiment. (ENU is ethyl nitrosourea).

Although the invention has been described hereabove as a process for the detection of mutations in one or more marker genes which have been introduced into the genome of a mammal by means of a vector, wherein the rescue and cloning of the methylated vector and the marker genes contained therein requires the use of a restriction negative host, the invention is generally applicable with any process for the rescue and cloning of DNA which may be methylated. The conventional process of cloning genomic DNA fragments does not use completely restriction-negative hosts. As a result thereof, the library of cloned fragments will not be complete, i.e. will not comprise the heavily methylated parts of the mammalian genome. The present invention solves this problem by using a restriction-negative host for the rescue and cloning of mammalian DNA which will result in a more complete collection of genomic DNA fragments.

In a broad sense, the invention therefore provides a process for the rescue and cloning of a DNA fragment wherein a vector containing said DNA fragment is multiplied in a suitable bacterial host, characterized by using as the bacterial host, a bacterial strain which is incapable of host restriction.

Although any bacterial species for which a suitable cloning vehicle is available may be used, a preferred embodiment of the invention is characterized by using as the bacterial host, an *Escherichia coli* strain which is incapable of host restriction. As an example of a preferred *Escherichia coli* strain which is incapable of host restriction, *Escherichia coli* C strains should be mentioned.

A preferred embodiment of the present invention is characterized by using as the vector, a bacteriophage vector which is a suitable cloning vehicle for the bacterial host concerned, the step of in vitro packaging into phage coats being performed by means of a phage packaging extract obtained from a bacterial strain which is incapable of host restriction.

Another, less preferred embodiment of the invention is characterized by using as the vector, a plasmid vector which is a suitable cloning vehicle for the bacterial host concerned.

A preferred process for the rescue and cloning of a DNA fragment wherein a vector containing said DNA fragment is multiplied in a suitable bacterial host is characterized by using an *Escherichia coli* strain which is incapable of host restriction as the bacterial host and a bacteriophage lambda vector as the vector, the step of in vitro packaging into phage coats being performed by means of a phage packaging extract obtained from an *Escherichia coli* strain which is incapable of host restriction. Again, it is preferred to use *Escherichia coli* C strains incapable of host restriction as bacterial host and source of the phage packaging extract, respectively.

The invention further provides a process for detecting mutations in one or more marker genes introduced into a mammalian genome by means of a vector, which process comprises isolating DNA from cells of a transgenic mammal or from mammalian cells, recovering the vector from said DNA, multiplying the vector in a suitable bacterial host which is deficient with respect to at least one of the marker genes, and testing marker gene expression, characterized by using as the bacterial host, a bacterial strain which is incapable of host restriction. Preferably, an *Escherichia coli* strain which is incapable of host restriction, such as an *Escherichia coli* C strain, is used as the bacterial host.

A preferred embodiment of the present invention is characterized by using as the vector, a bacteriophage vector which is a suitable cloning vehicle for the bacterial host concerned, the step of in vitro packaging into phage coats being performed by means of a phage packaging extract obtained from a bacterial strain which is incapable of host restriction.

An alternative process according to the invention is characterized by using as the vector, a plasmid vector which is a suitable cloning vehicle for the bacterial host concerned.

More in particular, the invention provides a process for detecting mutations in one or more marker genes introduced into a mammalian genome by means of a vector, which process comprises isolating DNA from cells of a transgenic mammal or from mammalian cells, recovering the vector from said DNA, multiplying the vector in a suitable bacterial host which is deficient with respect to at least one of the marker genes, and testing marker gene expression, which process is characterized by using an *Escherichia coli* strain which is incapable of host restriction as the bacterial host and a bacteriophage lambda vector as the vector, the step of in vitro packaging into phage coats being performed by means of a phage packaging extract obtained from an *Escherichia coli* strain which is incapable of host restriction.

Again, it is preferred to use *Escherichia coli* C strains incapable of host restriction as bacterial host and source of the phage packaging extract, respectively.

A highly preferred embodiment of the present invention is characterized in that the DNA isolated from cells of a transgenic mammal or mammalian cells is pre-purified by fragmenting the DNA by means of a restriction enzyme which does not have a cutting site within the vector, separating the resulting fragments on the basis of a suitable criterion, such as differences in size, and collecting fragments comprising the vector, whereafter the vector is recovered from said pre-purified DNA.

A preferred process according to the invention for detecting mutations in one or more marker genes introduced into a mammalian genome by means of a vector, which process comprises isolating DNA from cells of a transgenic mammal or from mammalian cells, recovering the vector from said DNA, multiplying the vector in a suitable bacterial host which is deficient with respect to at least one of the marker genes, and testing marker gene expression, is characterized in that an *Escherichia coli* strain which is incapable of host restriction is used as the bacterial host, a bacteriophage lambda vector having a size of at least 30 kb is used as the vector, at least 3 copies of said vector are integrated in the mammalian genome in a head-to-tail arrangement, the step of in vitro packaging into phage coats is performed by means of a phage packaging extract obtained from an *Escherichia coli* strain which is incapable of host restriction, and the DNA isolated from cells of the transgenic mammal or the mammalian cells is pre-purified by fragmenting the DNA by means of a restriction enzyme, such as XbaI, which does not have a cutting site within the vector but does have such a large number of cutting sites in the mammalian genome that it is capable of generating fragments having an average size below 10 kb, separating the resulting fragments on the basis of their size differences, and collecting the larger fragments comprising the vector. It is preferred to use *Escherichia coli* C strains incapable of host restriction as bacterial host and source of the phage packaging extract, respectively. It is further preferred that at least 10 copies of the bacteriophage lambda vector are integrated in the mammalian genome in a head-to-tail arrangement.

An alternative process according to the invention for detecting mutations in one or more marker genes introduced into a mammalian genome by means of a vector, which process comprises isolating DNA from cells of a transgenic mammal or from mammalian cells, recovering the vector from said DNA, multiplying the vector in a suitable bacterial host which is deficient with respect to at least one of the marker genes, and testing marker gene expression, is characterized in that an *Escherichia coli* strain which is incapable of host restriction is used as the bacterial host, the vector integrated in the mammalian genome is a plasmid vector flanked by restriction enzyme cutting sites which do not occur within the vector, and the vector is recovered by fragmenting the DNA isolated from cells of the transgenic mammal or the mammalian cells by means of said restriction enzyme and ring closure. As an example thereof, the invention provides a process for detecting mutations in one or more marker genes introduced into a mammalian genome by means of a vector, which process comprises isolating DNA from cells of the transgenic mammal or from mammalian cells, recovering the vector from said DNA, multiplying the vector in a suitable bacterial host which is deficient with respect to at least one of the marker genes, and testing marker gene expression, which process is characterized in that an *Escherichia coli* strain which is incapable of host restriction is used as the bacterial host, the vector integrated in the mammalian genome is a plasmid vector having a size of not more than 10 kb flanked by restriction enzyme cutting sites which do not occur within the vector and occur in such a small number in the mammalian genome for being capable of generating fragments having an average size above 20 kb, such as NotI restriction sites, and the DNA isolated from cells of the transgenic mammal or the mammalian cells is pre-purified by fragmenting the DNA by means of said restriction enzyme, separating the resulting fragments on the basis of their size differences and collecting the smaller fragments comprising the vector.

The invention can be directly applied in the efficient cloning of methylated DNA by the use of bacteriophage lambda vectors as cloning vehicles, packaging extracts derived from host restriction-negative *E. coli* strains, such as *E. coli* C and the same or comparable *E. coli* strains for plating. A second major application follows automatically and involves the testing of suspected agents for carcinogenicity. Shortly after treatment (e.g., after a few hours or a few days) the effect of the suspected agent, in terms of mutation frequency, can be directly studied in DNA from different organs and tissues of the treated transgenic animals, such as mice. Highly qualified staff is not required for this. Besides, the nature of the mutations can be determined in a relatively simple manner, because in this system the mutated lacZ gene is already cloned. When studying endogenous genes, such HPRT, it is always necessary first to obtain the mutated gene in pure condition. In the present case, each plaque is a small reservoir of lacZ genes which can be easily cultured further. The nucleotide sequence of the lacZ gene can now directly be determined by means of classical methods.

Besides the Ames test and the chemical structure of the suspected agent, the transgenic mouse model here described could well be a so desired third (in vivo) test (for a discussion of this problem, see Ashby and Tennant, 1988 and Hay, 1988). The introduction of the present invention as third test saves expenses, because it will then be necessary less often to make use of prolonged animal tests and of expensive veterinary pathologists. Introduction thereof also implies fewer inconveniences for the animals used, while the number of animals can be strongly reduced. All these factors make the present invention a suitable candidate for a third short-term test for chemicals suspected of carcinogenicity.

An important third field of application related to the second is the use of the above described transgenic mouse model for testing the potentially protective effect of certain agents. Although the prevention of unnecessary exposure to potentially carcinogenic agents is of course always preferred to protective steps, circumstances making said exposure inevitable are imaginable indeed. A simple example is the deliberate exposure of repair crews to much too high doses of carcinogenic agents in case of industrial accidents (or radiation in, e.g., accidents with nuclear power plants). The availability of pharmaceutics having a protective effect against injury to the heritable material could bring relief here. However, also apart from this type of extreme conditions, injury to the heritable material is not always avoidable. For instance, there are indications that in many houses the amount of background radiation is extremely high, which makes protection desirable. On the other hand, in some latitudes the amount of ultraviolet light is so high that the risk of cutaneous cancer considerably increases. In a more general sense, it may be said that exposure to (unduly) high doses of DNA-injuring factors will increasingly become an inevitable reality of everyday life. In this connection it is relevant to aim at protection, e.g., by adding protective agents to the diet. Although it is suggested that certain diet factors, such as vitamin c, SOD (superoxide dismutase), carotene, etc. would indeed protect against DNA-injuring agents and as a result perhaps against cancer, this has never been demonstrated convincingly so far. By means of the present invention certain pharmaceutics can be tested for their ability to protect the individual against injury to its heritable material. This can be done in practice by treating the above described transgenic mice with DNA-injuring agents in the presence and the absence of the agent to be tested. A possible beneficial effect thereof in the form of a reduction of the mutation frequency can then be rapidly determined by recovering a large number of vectors from different organs and tissues of the animals in question.

DESCRIPTION OF EXPERIMENTS

Figure 1:
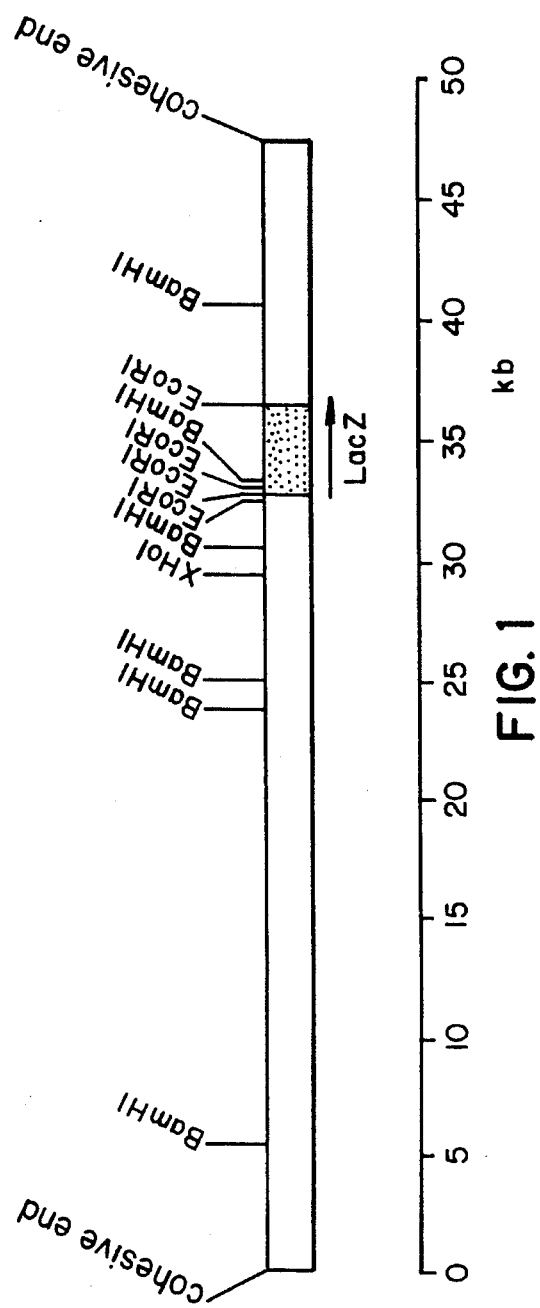
FIG. 1 is a diagrammatic representation of the bacteriophage lambda vector gt101acZ described in the experimental part.

The bacteriophage lambda vector used is shown in FIG. 1. This vector, lambda gt101acZ, was obtained by cloning the lacZ gene at the EcoRI site of the commercially available bacteriophage lambda vector gt10 (Promega B.V., P.O.B. 391, 2300 AJ Leiden). The map only indicates the EcoRI sites, the BamHI sites and the XhoI site. The vector had no recognition sites for the enzyme XbaI. This is an important characteristic because this enzyme has a recognition site in total genomic mammal DNA at an average of 5000 base pairs. This property will be dealt with later.

The above vector is transferred to the germ line of mouse strain CD2, the F1 of BALB/C×DBA/2, by means of microinjection. These two strains form part of the colony of rodents of the Institute for Experimental Gerontology TNO. About 150 copies of the vector were injected into one of the two pronuclei of a fertilized ovum of a CD2 mouse. A detailed description of the protocol suitably followed is contained in Hogan et al. (1986).

Figure 2:
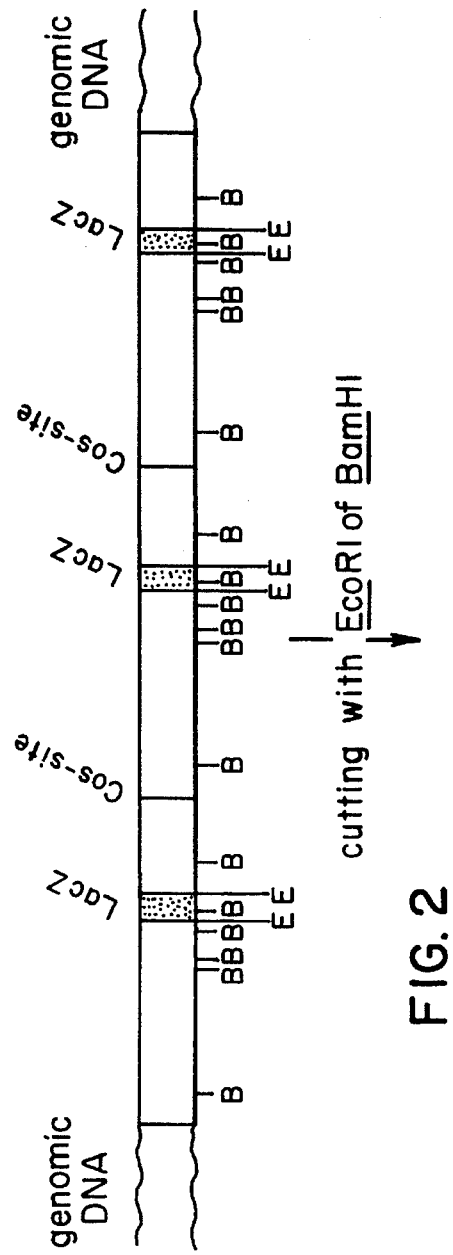
FIG. 2 is a diagrammatic representation of the head-to-tail arrangement of vector copies in the genome of the transgenic mice.

FIG. 2 shows the expected head-to-tail arrangement of the vectors after integration in the mouse genome. It is known from the literature that after microinjection of DNA fragments into the nucleus of a fertilized mouse ovum these generally integrate in a head-to-tail arrangement at random places (Brinster et al., 1987). As FIG. 2 shows, two half cos sites will form one whole cos site after head-to-tail integration. This is essential, since for the recovery of one vector requires the presence of a whole cos site at both sides of the vector; only whole cos sites are recognized and cut and cut by the terminase enzyme in the packaging extract. The phage DNA between two cos sites is then packaged into phage coats. Consequently, at least three vectors integrated in a head-to-tail arrangement are required to recover one vector from total genomic DNA. FIG. 2 shows that, in case of head-to-tail integration in two or more copies, after cutting of total genomic mouse DNA there must be formed a BamHI fragment of 12.6 kb containing one intact cos site. Besides, 5 other BamHI fragments are formed. Cutting with EcoRI gives three fragments, one of which represents the lacZ.

Figure 3:
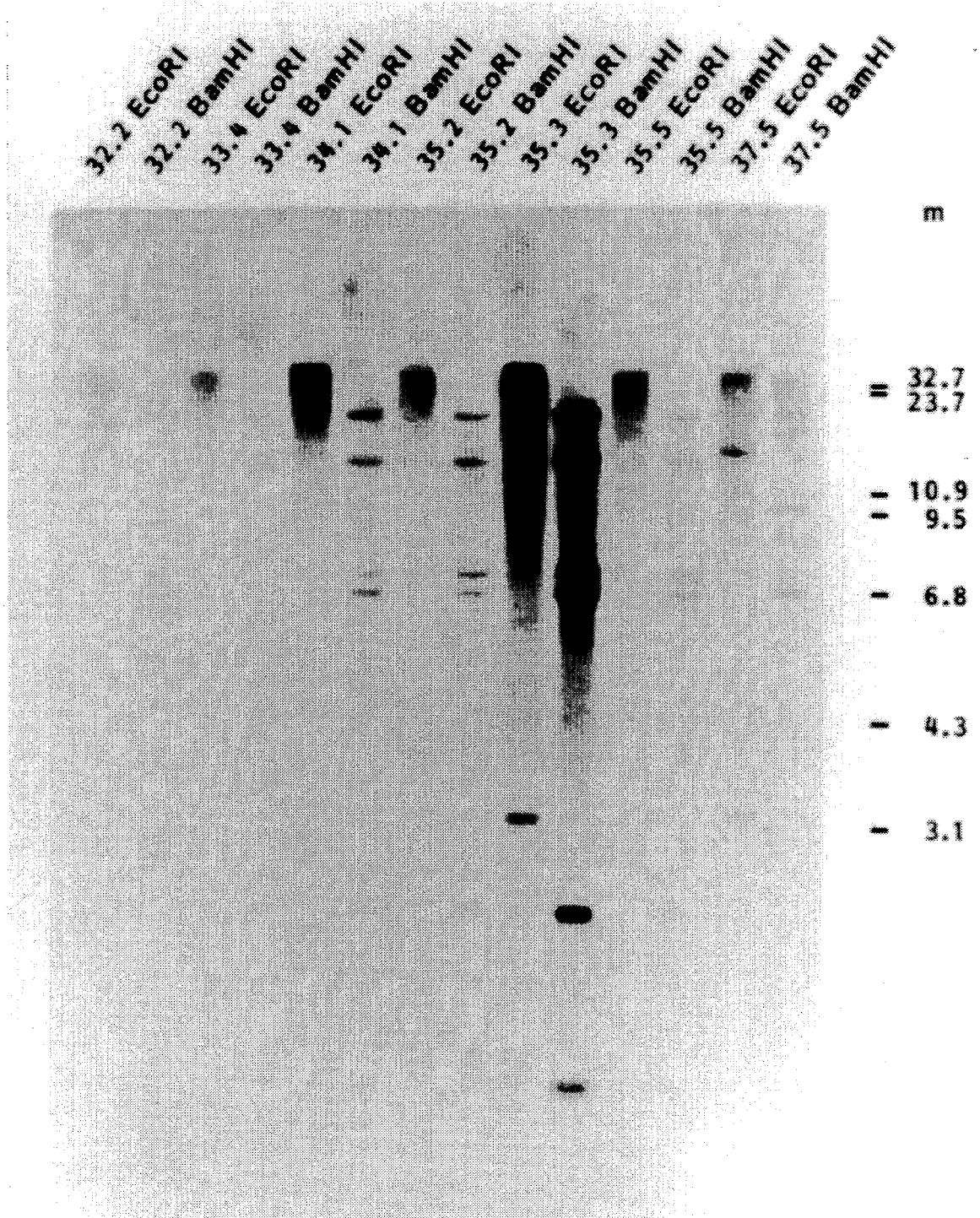
FIG. 3 is a diagrammatic representation of an autoradiogram after Southern blotting of DNA from different transgenic mice, cut with BamHI or EcoRI.

FIG. 3 shows that, as anticipated, the vector is integrated in a head-to-tail arrangement in a plurality of copies; only in two of the 7 cases one copy was found present. This could be demonstrated by isolating DNA of the newly born transgenic mice from the tail and then analyzing this by using the Southern method. The DNA was always cut with BamHI and (separately) with EcoRI. The autoradiogram of FIG. 3 shows that in mice 33.4, 34.1, 35.2, 35.3 and 35.5 the sixth BamHI band is clearly present. The differences of intensity show that the copy number in which the vector (head-to-tail) is integrated varies greatly. In transgenic mouse 35.5 this number is 3.

In theory, it should be possible to rescue about 17000 vectors from 1 µg total genomic DNA, starting from a packaging efficiency of $10^9$ per µg pure vector[the length of the vector (about $5\times10^4$) divided by the length of the total mammalian genome (about $3\times10^9$) multiplied by the packaging efficiency (about $10^9$ per µg pure vector using the present commercially available packaging extracts)]. This calculation also starts from 3 integrated vectors per cell genome (so only one of them can be rescued).

However, contrary to what may be expected in theory, it can be derived from the results of others with lambda vectors integrated in the genomic DNA of cell lines that the packaging efficiency is not much higher than a few plaques per µg total genomic DNA. The reason for this was unknown. Rescue efficiencies of integrated plasmid vectors are in the same order.

Attempts to recover the vectors integrated by us in the mouse genome directly from chromosomal DNA of different organs and tissues resulted in the first instance in only a few plaques per µg DNA. Accordingly, our findings were not different from the above results of others. For isolating total chromosomal DNA from different organs and tissues these were first homogenized in a Dounce homogenizer and then incubated overnight in 5 volumes 100 mM EDTA, 50 mM Tris-Cl, pH 7.5, 100 mM NaCl, 1% SDS, 200 µg/ml proteinase K at 65° C. Then the solution was mixed with ⅕ volume 8 M potassium acetate and stored on ice for 30 minutes. After 1×chloroform extraction the DNA was precipitated with 1 volume ice cold ethanol. The DNA was rinsed with 70% ethanol and then solubilized in TE buffer (10 mM Tris-Cl, pH 7.5, 0.1 mM EDTA). In all the experiments described below this isolation procedure was followed.

For packaging in vitro use is made of a procedure which is standard in many laboratories (see Maniatis et al., 1982). The procedure is based on mixing the lambda vectors (in our case the total genomic mouse DNA with the lambda vectors therein) with the packaging extract which provides for packaging each vector into a phage coat. After mixing with a large excess of bacteria (the host) these are grown on a nutrient medium. The bacteria which are first allowed the time to grow are all slowly but surely infected by the phages. This becomes visible through a large number of clear areas in the closed bacterial lawn. Each clear area (which is very small at the beginning but constantly increases until the whole bacterial lawn has turned clear) corresponds to one lambda vector. Because our vector contains the bacterial gene lacZ, the clear areas must be blue.

However, attempts made by means of this protocol to package lambda vectors integrated in the genome are only rare. In nearly all cases packaging is applied when genomic DNA fragments are cloned in pure vectors. These are commercially available and are grown by the manufacturer on bacteria and isolated therefrom by means of relatively simple methods in pure form. In our case the vectors are integrated at one or more places in the mouse genome and cannot be isolated therefrom in a simple manner.

Figure 4:
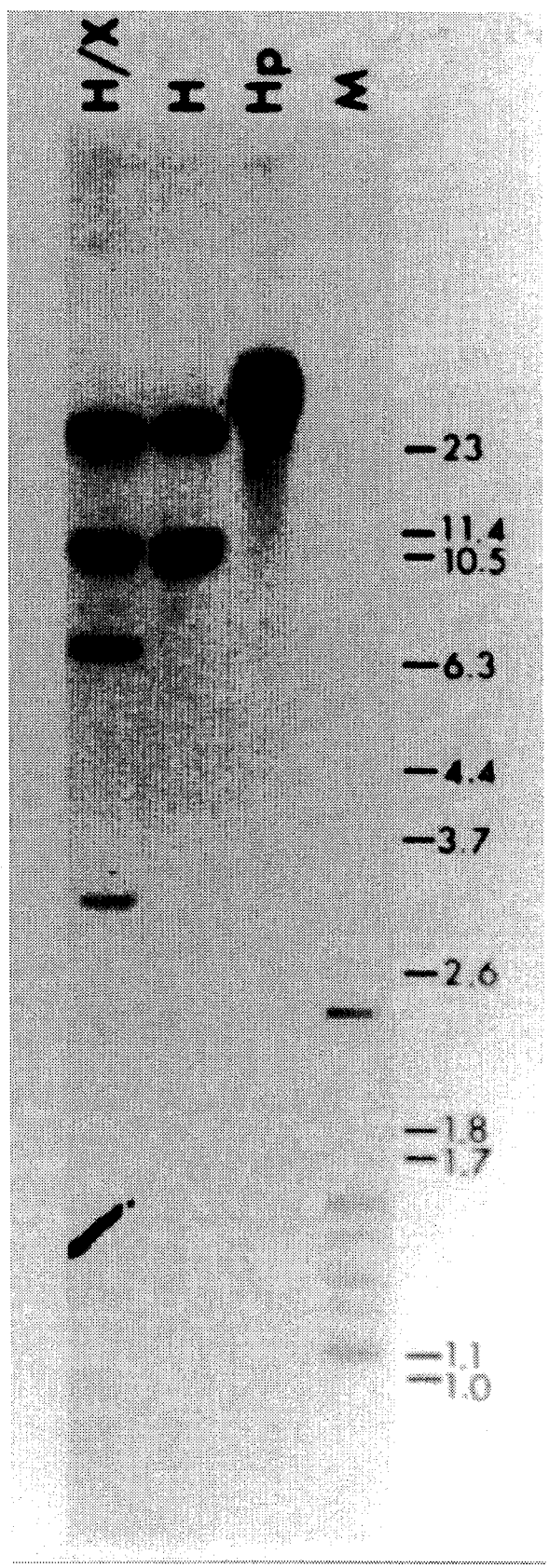
FIG. 4 is a diagrammatic representation of an autoradiogram after Southern blotting of DNA from the liver of transgenic mouse 35.5, cut with Hind III(H), Hind III/XhoI (H/X), HpaII (Hp) or MspI (M); $^{32}$P-labeled lambda-gt10 lacZ is used as a probe.

A further analysis of the lambda vectors integrated in the mouse genome by means of so-called isoschizomeric restriction enzymes (two different restriction enzymes both recognizing the same site, except when this is methylated) taught that in each tested mouse the lambda vectors were fully methylated. The audioradiogram (FIG. 4) showed that DNA from transgenic mouse 35.5 is cut by MspI but not by HpaII. Like MspI, HpaII also recognizes CCGG sites. However, if the middle C carries a methyl group, HpaII is not capable of cutting but MspI is. The conclusion therefore is that the lambda vectors integrated in the mouse genome are highly (perhaps even completely) methylated. This conclusion was confirmed by results obtained with the methylation-sensitive restriction enzyme XhoI. As shown in FIG. 4, this enzyme is not capable of completely cutting the band of about 10 kb generated by HindIII. In FIG. 4, M refers to MspI, Hp to HpaII, H to HindIII and X to XhoI.

It is known from the literature that most of the bacterial strains are capable of making entering "foreign" DNA innocuous by cutting it into pieces. The enzymes concerned are then guided by certain methylation patterns. Our assumption that this so-called host restriction might be the reason for the very low packaging efficiency of the lambda vectors integrated in the mouse DNA (and completely methylated) was tested by means of an experiment with different $E.\ coli$ hosts, one of which was in no way capable of host restriction (the $E.\ coli$ C strain) and others only partially ($E.\ coli$ K12 Y1090 (MCR-A$^-$,MCR-B$^+$) and $E.\ coli$ K12 KA802 (MCR-A$^-$,MCR-B$^-$). The $E.\ coli$ C strain is normally not used in packaging experiments. As far as we know, lacZ$^-$ variants are not known either. For our purposes the strain must lack the entire lacZ gene so that mutants can be recognized as uncoloured plaques For if the host bacteria themselves are lacZ$^+$, all plaques are coloured, even the mutants.

The following procedure was followed in order to obtain an $E.\ coli$ C variant which is lacZ$^-$. A nutrient medium on which $E.\ coli$ C bacteria were plated was irradiated with 25 Gy gamma radiation, which is known to be mutagenic. The nutrient medium contained X-gal. The normal bacteria (the "wild types") will give blue colonies because, normally speaking, bacteria have an active lacZ gene. However, lacZ mutants, if any, will be colourless. On the basis of this criterion two colourless colonies were found with bacteria irradiated with gamma rays, which colonies gave blue plaques when used as a host for lacZ-containing lambda vectors. Plating with lambda vectors which did not contain lacZ gave only colourless plaques, which confirmed the mutant status of the newly generated bacterial strain.

After packaging the lambda vectors integrated in the mouse DNA a large number of (blue) plaques was only found with the $E.\ coli$ C strain (Table 1). The highest efficiency, namely about 9,000 plaques per μg total genomic mouse DNA, was obtained with transgenic mouse strain 20.2, the vector being incorporated in about 80 copies. This is still lower than the packaging efficiency feasible in theory. However, it should be considered that the quality of total genomic DNA isolated from tissues is still many times lower than that of purified DNA on which all calculations are based. Nevertheless, the conclusion that can be drawn from this series of experiments is that efficient packaging of lambda vectors integrated in total genomic DNA is certainly possible, but only if the host used is an $E.\ coli$ strain incapable of host restriction. Because the packaging extracts themselves are also made from bacteria it is absolutely necessary to use only those extracts which have been made from host restriction-negative $E.coli$ strains, such as $E.\ coli$ C strains. The same applies to the genetic cloning of methylated DNA; only host restriction-negative $E.coli$ strains, such as $E.coli$ C, can be used, both as source of the packaging extract and for plating.

Starting from the above lambda-containing transgenic mouse strains and the packaging efficiencies obtained with $E.\ coli$ C extracts and strains, attempts have then be made to increase as much as possible the total number of vectors to be recovered. In this connection the limiting factor is not the amount of available genomic DNA (2 mg DNA can be easily isolated from, e.g., a whole liver of a mouse) but the amount of DNA that can be added to a certain amount of packaging extract. In view of the price of this commercially available extract a scale-up is a very expensive affair which makes the application of in vitro packaging in mutation analyses by means of our mouse model commercially unattractive.

In order to avoid the above problems, it seemed to us necessary, so to speak, to pre-purify the integrated vector(s), so that the ratio of vector to redundant mouse DNA is much more favourable. This is not easy because, in general, vectors have no special characteristics by which they can be separated preparatively from mammalian DNA. As stated before, with the transgenic mice prepared by us the vector is integrated in a number of copies in a head-to-tail arrangement. We conceived that this phenomenon can be used to increase the recovery efficiency of integrated vectors. If it is ensured that the injected vector lacks a recognition site for a certain restriction enzyme, this will result with transgenic mice and/or cell lines in a very long DNA fragment without the restriction site concerned. If, e.g., 30 copies of the vector are integrated in tandem in head-to-tail arrangement, this fragment will have a length of 50,000×30=1,500,000 base pairs. If with total genomic mammalian DNA the restriction enzyme concerned gives fragments having an average size of about 5000 base pairs, a fragment of 1.5 millions of base pairs can easily be separated therefrom.

In order to test the above pre-purification strategy and to determine whether cutting of total chromosomal mouse DNA with XbaI indeed resulted in one very large fragment together with many fragments having an average size of about 5000 base pairs, use was made of Field Inversion Gel Electrophoresis (FIGE). This technique renders it possible to properly separate DNA fragments having a length up to about 1 million of base pairs.

Figure 5:
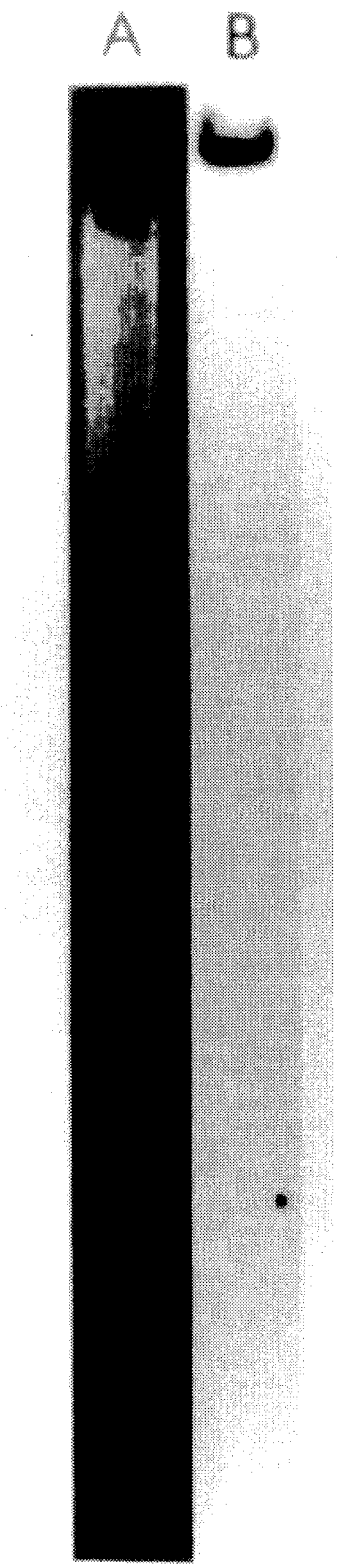
FIG. 5 shows the results of preparative FIGE of DNA of transgenic mice, which DNA is cut with XbaI lane A shows the result of ethidium bromide staining and lane B shows the result of hybridization analysis with radioactively labeled vector.

Thus, about 100 μg total chromosomal DNA from the brain (and later also from other organs) were cut with 400 units of Xba I under conditions as described by the manufacturer (BRL). The digest was then subjected to Field Inversion Gel Electrophoresis (the equipment required was obtained from Hoefer Scientific Instruments, P.O.B. 77387, San Francisco, Calif. 94107-9985) for 4 hours at 250 Volt (forward: 0.6 sec.; reverse: 0.2 sec; ramp: 0.0) at 14° C. in 1×TBE buffer (TBE=89 mM Tris-Cl, 89 mM boric acid, 2 mM EDTA). After electrophoresis the gel was coloured in ethidium bromide, after which the low molecular weight fraction manifested itself as a smear having an average length of 5 kb (see FIG. 5, lane A). Hybridization analysis of this gel pattern with the radioactively labeled vector itself as a probe showed a select band having a fragment length of more than 500,000 base pairs (FIG. 5, lane B). This band therefore represents the bacteriophage lambda vectors.

The high molecular vector-containing fragments were isolated from the gel by means of electroelution, precipitated with ethanol, solubilized in TE buffer, added to the *E.coli* C packaging extract and then plated with *E. coli* C as a host. While it was first possible by means of 10 µl packaging extract (value: about NLG. 100.-) to recover about 9,000 plaques from about 1 µg total chromosomal DNA of transgenic mouse 20.2, it now turned out that by means of the same amount of packaging extract about 1,400,000 plaques could be obtained from about 100 µg total chromosomal DNA of the same transgenic mouse strain, which means a great saving.

Finally, the usability of the prepared transgenic mouse strains as mutation models for testing potentially carcinogenic agents was subjected to a test. First, the background mutation frequency was determined in vectors, pre-purified and packaged, according to the protocol described in the invention, from genomic DNA of brain and liver of transgenic mice (strain 20.2). The results obtained indicate background mutation frequencies lower than $10^{-5}$ (Table 2). Comparable results were obtained with strain 40.6.

To demonstrate the applicability of this system for testing the mutagenicity of chemicals in vivo, adult female transgenic mice were treated with ethylnitrosourea (ENU). Mutation frequencies in the lambda-gt10LacZ shuttle vector rescued from different organs and tissues of control and ENU-treated transgenic mice were determined as the ratio of colourless versus blue plaques.

To discriminate between mutations arisen in the mice and those that theoretically could be formed after packaging in the bacteria, two animals (treated with 100 mg ENU per kg body weight) were sacrificed already 1 day after treatment. Vectors isolated from organs of these mice should still contain, so shortly after treatment, ENU-induced DNA lesions, which could give rise to mutations in the bacteria. However, no increase in the mutation frequency was observed in brain and liver of these animals (Table 2), suggesting that induced mutations detected in this system find their origin predominantly in the mouse.

Figure 6:
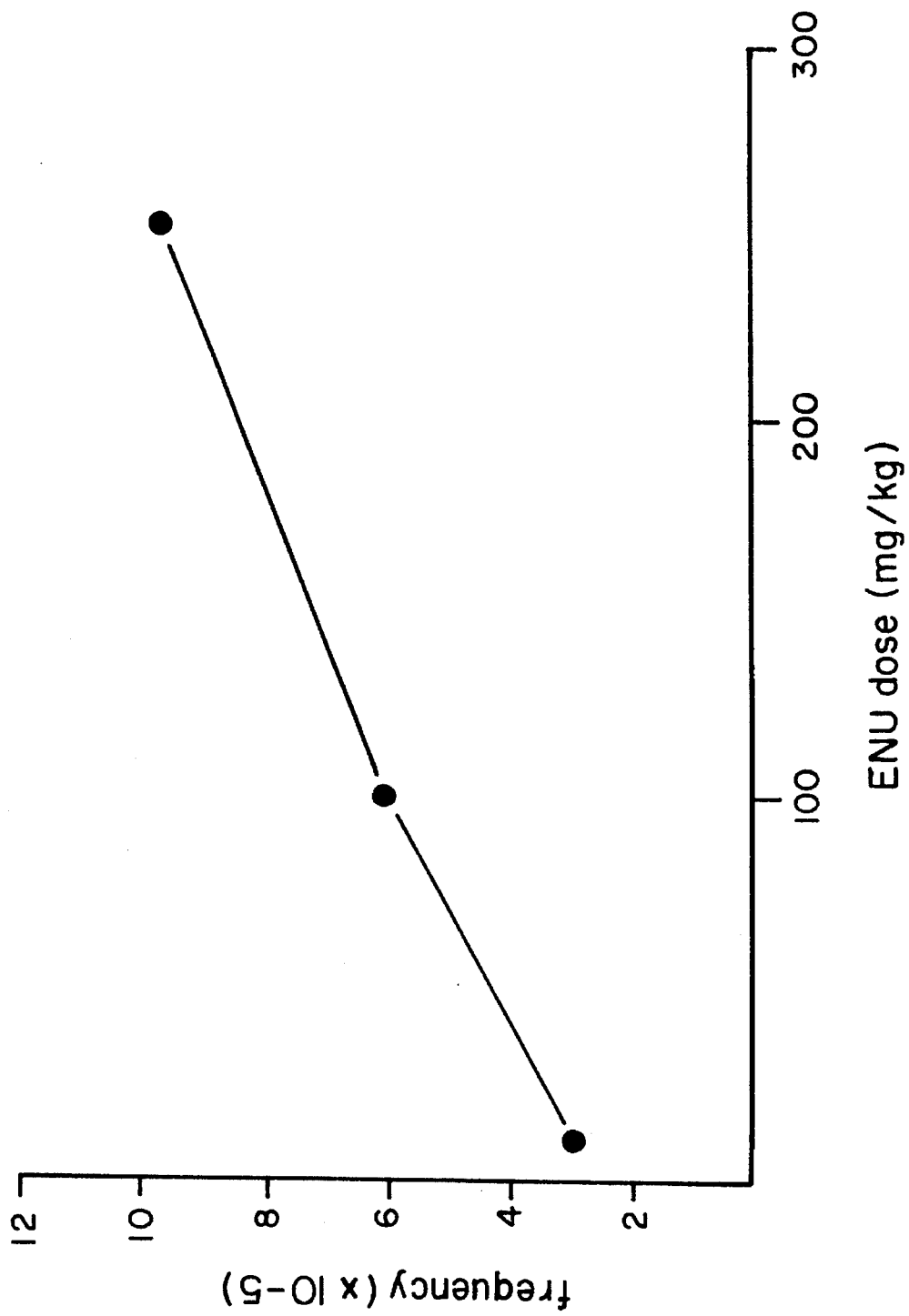
FIG. 6 shows the frequency of colourless plaques (mutation frequency) as a function of the dose of ethyl nitrosourea (ENU).

All other animals were sacrificed at 7 days after treatment and the results obtained reveal an increase of the mutation frequency in an organ-specific way; mutation frequencies at the highest dose were considerably higher in the brain than in the liver (Table 2). Mutation frequencies were found to be dose-dependent; at a dose as low as 10 mg ENU per kg body weight an increase in mutation frequencies relative to the background was still clearly observed (FIG. 6 showing the average mutation frequencies in the brain).

IV. References

Albertini, R. J. et al. Proc. Natl. Acad. Sci. USA 79, 6617 (1982)
Albertini, R. J. et al. Nature 316, 369 (1985)
Ames, B. N. et al. Proc. Natl. Acad. Sci. USA 70, 2281 (1973)
Ashby, J and Tennant, RW Mutation Res 204, 17–115 (1988)
Dubridge, R. B. and Calos, M. P. Mutagenesis 3, 1–9 (1988)
Glazer, P. M. et al. Proc. Natl. Acad. Sc. USA 83, 1041–1044 (1986)
Hay A, Nature 332, 782–783 (1988)
Hogan, B. et al. Manipulating the Mouse Embryo: A Laboratory Manual, Cold Spring Harbor Laboratory, Cold Spring Harbor, N.Y. (1986)
Lehman, A. R. Mutation Res. 150, 61–67 (1985)
Lindenmaier, W. et al. Nucleic Acids Res. 10, 1243 (1982)
Lohman, P. H. M. et al. Mutation Res. 181, 227–234 (1987)
Maniatis, T. et al. Molecular Cloning: A Laboratory Manual, Cold Spring Harbor Laboratory, Cold Spring Harbor, N.Y. (1982)
Palmiter, R. D. and Brinster R. L. Annu.Rev. Genet. 20, 465 (1987)
Raleigh, E. A. and Wilson, G. Proc. Natl. Acad. Sci. USA 83, 9070 (1986)
Vijg, J. and Uitterlinden, A. G. Mech. Ageing Dev. 41, 47–63 (1987)
Zeiger E et al. Cancer Res. 47, 1287 (1987)
Featherstone, T. et al. Mutation Res. 179, 215 (1987)

TABLE 1

RESCUE EFFICIENCY OF LAMBDA-GT10LACZ SHUTTLE VECTOR FROM 1 µg TOTAL GENOMIC DNA OF TRANSGENIC MOUSE STRAIN 20.2.

| In vitro packaging extract | Host strain | | |
|---|---|---|---|
| | *E. coli* K12 Y1090 (McrA−, McrB+) | *E. coli* K12 KA802 (McrA−, McrB−) | *E. coli* C |
| *E. coli* K12-derived | 0 pfu | 0 pfu | 2 pfu |
| *E.coli* C-derived | 0 pfu | 3 pfu | 9100 pfu |

TABLE 2

Mutation frequencies in the lambda-gt10LacZ shuttle vector rescued from brain and liver of control and ENU-treated transgenic mice.

| Organ | ENU dose (mg/kg) | number of phages analyzed | number of mutants | mutation frequency |
|---|---|---|---|---|
| brain | 0 | 138,816 | 0 | nd |
| brain[1] | 0 | 81,792 | 0 | nd |
| brain[2] | 100 | 92,608 | 0 | nd |
| brain[2] | 100 | 80,960 | 0 | nd |
| brain | 10 | 198,208 | 3 | $1.5 \times 10^{-5}$ |
| brain | 100 | 167,296 | 5 | $3.0 \times 10^{-5}$ |
| brain | 100 | 204,032 | 7 | $3.4 \times 10^{-5}$ |
| brain | 250 | 197,312 | 13 | $6.7 \times 10^{-5}$ |
| brain | 250 | 67,832 | 5 | $7.4 \times 10^{-5}$ |
| liver | 0 | 168,160 | 0 | nd |
| liver[1] | 0 | 148,464 | 1 | $0.7 \times 10^{-5}$ |
| liver[2] | 100 | 151,232 | 0 | nd |
| liver[2] | 100 | 146,336 | 1 | $0.7 \times 10^{-5}$ |
| liver | 10 | 121,632 | 0 | nd |
| liver | 100 | 141,088 | 5 | $3.5 \times 10^{-5}$ |
| liver | 100 | 95,808 | 3 | $3.1 \times 10^{-5}$ |
| liver | 250 | 137,760 | 3 | $2.1 \times 10^{-5}$ |
| liver | 250 | 141,488 | 2 | $1.4 \times 10^{-5}$ |

Each entry represents data on a single animal. 1) treated with DMSO only 2) mice sacrificed 1 day after treatment 3) nd = not detectable

We claim:

1. A process for the high efficiency rescue and cloning of a DNA fragment from genomic mammalian DNA comprising the steps of preparing a vector containing the DNA fragment, followed by multiplying said vector containing said DNA fragment in a suitable bacterial host wherein said bacterial host is selected as being incapable of host restriction and further is selected as being capable of rescuing 900,000 copies of said fragment per 100 micrograms of genomic mammalian DNA when said 100 micrograms of genomic mammalian DNA derives from a mouse genome in which said fragment has a copy number of about 80 and said about 80 copies are present in a head-to-tail arrangement to effect rescue and cloning of said DNA fragment at an efficiency level defined as that efficiency of which a bacterial host, selected as being capable of rescuing 900,000 copies of said fragment per 100 micrograms of genomic mammalian DNA when said 100 micrograms of genomic mammalian DNA derives from a mouse genome in which said fragment has a copy number of about 80 and said about 80 copies are present in a head-to-tail arrangement, is capable.

2. The process according to claim 1 wherein said bacterial host is an *Escherichia coli* strain.

3. The process according to claim 1 wherein said bacterial host is an *Escherichia coli* C strain.

4. A process according to claim 1 wherein said vector is a bacteriophage vector obtained by means of a phage packaging extract derived from a bacterial host selected as being incapable of host restriction and further selected as being capable of rescuing 900,000 copies of said fragment per 100 micrograms of genomic mammalian DNA when said 100 micrograms of genomic mammalian DNA derives from a mouse genome in which said fragment has a copy number of about 80, said about 80 copies are present in a head-to-tail arrangement.

5. A process according to claim 1 wherein said vector is a plasmid.

6. A process for the rescue and cloning of a DNA fragment from genomic mammalian DNA wherein a vector containing said DNA fragment is multiplied in a first bacterial host, wherein said first bacterial host is selected as being incapable of host restriction and further is capable of rescuing 900,000 copies of said fragment per 100 micrograms of genomic mammalian DNA when said 100 micrograms of genomic mammalian DNA derives from a mouse genome in which said fragment has a copy number of about 80, said about 80 copies are present in a head-to-tail arrangement, further wherein said first bacterial host is an *Escherichia coli* strain, further wherein said vector is a bacteriophage lambda vector, and further wherein said bacteriophage lambda vector is obtained by means of a phage packaging extract derived from a second bacterial host incapable selected as being of host restriction and further selected as being capable of rescuing 900,000 copies of said fragment per 100 micrograms of genomic mammalian DNA when said 100 micrograms of genomic mammalian DNA derives from a mouse genome in which said fragment has a copy number of about 80, said about 80 copies are present in a head-to-tail arrangement, to effect rescue and cloning of the genomic mammalian DNA fragment.

7. The process according to claim 6 wherein each of said first bacterial host and said second bacterial host is an *Escherichia coli* C strain.

8. A process for detecting mutations in one or more marker genes introduced into a mammalian genome by means of a vector, which process comprises isolating DNA from cells of a transgenic mammal or from mammalian cells, recovering said DNA by means of a vector, multiplying said vector in a bacterial host which is deficient with respect to at least one of the marker genes, and testing marker gene expression for mutation, wherein said bacterial host is selected as being incapable of host restriction and further is capable of rescuing 900,000 copies of a fragment containing said vector per 100 micrograms of genomic mammalian DNA when said 100 micrograms of genomic mammalian DNA derives from a mouse genome in which said fragment has a copy number of about 80 and said about 80 copies are present in a head-to-tail arrangement, wherein said recovering and multiplying of said DNA is performed at an efficiency level defined as that efficiency of which a bacterial host, selected as being capable of rescuing 900,000 copies of said fragment per 100 micrograms of genomic mammalian DNA when said 100 micrograms of genomic mammalian DNA derives from a mouse genome in which said fragment has a copy number of about 80 and said about 80 copies are present in a head-to-tail arrangement, is capable.

9. The process according to claim 8 wherein said bacterial host is an *Escherichia coli* strain.

10. The process according to claim 8 wherein said bacterial host is an *Escherichia coli* C strain.

11. The process according to claim 8 wherein said vector is a bacteriophage vector obtained by means of a phage packaging extract derived from a bacterial host selected as being incapable of host restriction and further selected as being capable of rescuing 900,000 copies of said fragment per 100 micrograms of genomic mammalian DNA when said 100 micrograms of genomic mammalian DNA derives from a mouse genome in which said fragment has a copy number of about 80, and said about 80 copies are present in a head-to-tail arrangement.

12. The process according to claim 8 wherein said vector is a plasmid.

13. A process for detecting mutations in one or more marker genes introduced into a mammalian genome by means of a vector, which process comprises isolating DNA from cells of a transgenic mammal or from mammalian cells, recovering said DNA by means of a vector, multiplying said vector in a first bacterial host which is deficient with respect to at least one of the marker genes, and testing marker gene expression for mutation, wherein said first bacterial host is an *Escherichia coli* strain selected as being incapable of host restriction and further selected as being capable of rescuing 900,000 copies of a fragment containing said vector per 100 micrograms of genomic mammalian DNA when said 100 micrograms of genomic mammalian DNA derives from a mouse genome in which said fragment has a copy number of about 80, said about 80 copies are present in a head-to-tail arrangement, and further wherein said vector is a bacteriophage vector obtained by means of a phage packaging extract derived from a second bacterial host selected as being incapable of host restriction and further selected as being capable of rescuing 900,000 copies of said fragment per 100 micrograms of genomic mammalian DNA when said 100 micrograms of genomic mammalian DNA derives from a mouse genome in which said fragment has a copy number of about 80 and said about 80 copies are present in a head-to-tail arrangement.

14. The process according to claim 6 wherein each of said first bacterial host and said second bacterial host is an *Escherichia coli* C strain.

15. The process according to any of claims 8–14 characterized in that the DNA isolated from cells of the transgenic mammal or the mammalian cells is prepurified by fragmenting the DNA by means of a restriction enzyme which does not have a cutting site within the vector, separating the resulting fragments on the basis of a suitable criterion, such as differences in size, and collecting fragments comprising the vector, whereafter the vector is recovered from said prepurified DNA.

16. A process for detecting mutations in one or more marker genes introduced into a mammalian genome by means of a vector, which process comprises isolating DNA from cells of a transgenic mammal or from mammalian cells, recovering said DNA by means of a vector, multiplying said vector in a first bacterial host which is deficient with respect to at least one of the marker genes, and testing marker gene expression for mutation, wherein said first bacterial host is an *Escherichia coli* strain selected as being incapable of host restriction and further selected as being capable of rescuing 900,000 copies of a fragment containing said vector per 100 micrograms of genomic mammalian DNA when said 100 micrograms of genomic mammalian DNA derives from a mouse genome in which said fragment has a copy number of about 80, said about 80 copies are present in a head-to-tail arrangement, and further wherein said vector is a bacteriophage lambda vector obtained by means of a phage packaging extract derived from a second *Escherichia coli* bacterial host incapable selected as being of host restriction and further selected as being capable of rescuing 900,000 copies of said fragment per 100 micrograms of genomic mammalian DNA when said 100 micrograms of genomic mammalian DNA derives from a mouse genome in which said fragment has a copy number of about 80, said about 80 copies are present in a head-to-tail arrangement further wherein said bacteriophage lambda vector has a size of at least 40 kb, further wherein at least 3 copies of said vector are integrated in the genome of said transgenic mammal or said mammalian cells in a head to tail arrangement and further wherein said DNA is prepurified by fragmenting the DNA by means of the restriction enzyme XbaI, which does not have a cutting site within the vector but does have such a large number of cutting sites in the mammalian genome that it is capable of generating fragments having an average size below 10 kb, separating the resulting fragments on the basis of their size differences, and collecting the larger fragments comprising said vector.

17. The process according to claim 16 wherein each *Escherichia coli* strain is an *Escherichia coli* C strain.

18. The process according to claim 16 wherein at least 10 copies of said vector are integrated in the genome of said transgenic mammal or said mammalian cells in a head to tail arrangement.

19. A process for detecting mutations in one or more marker genes introduced into a mammalian genome by means of a vector, which process comprises isolating DNA from cells of a transgenic mammal or from mammalian cells, recovering the vector from said DNA, multiplying said vector in an *Escherichia coli* bacterial host incapable of host selected as being restriction and further selected as being capable of rescuing 900,000 copies of a fragment containing said vector per 100 micrograms of genomic mammalian DNA when said 100 micrograms of genomic mammalian DNA derives from a mouse genome in which said fragment has a copy number of about 80, said about 80 copies are present in a head-to-tail arrangement and testing marker gene expression for mutation, wherein said vector is further a plasmid vector flanked by restriction enzyme cutting sites which do not occur within the vector, and said vector is recovered by fragmenting the DNA isolated from cells of the transgenic mammal or the mammalian cells by means of a restriction enzyme specific for said restriction enzyme cutting sites and by ring closure, and wherein said recovering and multiplying of said vector is performed at an efficiency level defined as that efficiency of which a bacterial host, selected as being capable of rescuing 900,000 copies of said fragment per 100 micrograms of genomic mammalian DNA when said 100 micrograms of genomic mammalian DNA derives from a mouse genome in which said fragment has a copy number of about 80 and said about 80 copies are present in a head-to-tail arrangement, is capable.

20. A process for detecting mutations in one or more marker genes introduced into a mammalian genome by means of a vector, which process comprises isolating DNA from cells of a transgenie mammal or from mammalian cells, recovering said DNA by means of a vector, multiplying said vector in a first bacterial host which is deficient with respect to at least one of the marker genes, and testing marker gene expression for mutation, wherein said first bacterial host is an *Escherichia coli* strain selected as being incapable of host restriction and further selected as being capable of rescuing 900,000 copies of a fragment containing said vector per 100 micrograms of genomic mammalian DNA when said 100 micrograms of genomic mammalian DNA derives from a mouse genome in which said fragment has a copy number of about 80, said 80 copies are present in a head-to-tail arrangement, and further wherein said vector is a plasmid vector having a size of not more than 10 kb flanked by NotI restriction enzyme cutting sites which do not occur within said vector and which occur in such a small number in the genome of said transgenic mammal or mammalian cells that they are capable of generating DNA fragments having an average size greater than 20 kb, and further wherein the DNA isolated from the cells of said transgenic mammal or said mammalian cells is prepurified by fragmenting said isolated DNA with a restriction enzyme specific for said NotI restriction sites, separating the resulting fragments on the basis of their size differences and collecting the small fragments comprising said vector and wherein said recovering and multiplying of said DNA is performed at an efficiency level defined as that efficiency of which a bacterial host, selected as being capable of rescuing 900,000 copies of said fragment per 100 micrograms of genomic mammalian DNA when said 100 micrograms of genomic mammalian DNA derives from a mouse genome in which said fragment has a copy number of about 80 and said about 80 copies are present in a head-to-tail arrangement, is capable.

* * * * *

UNITED STATES PATENT AND TRADEMARK OFFICE
CERTIFICATE OF CORRECTION

PATENT NO.  : 5,470,706
DATED       : November 28, 1995
INVENTOR(S) : Jan Vijg and Jan A. Gossen Page 1 of 3

It is certified that error appears in the above-indentified patent and that said Letters Patent is hereby corrected as shown below:

Column 5 Line 16 "Not I)" should read --NotI)--.

Column 5 Line 46 "restriction negative" should read --restriction-negative--.

Column 8 Line 22 after "such" insert --as--.

Column 8 Line 32 after "as" insert --the--.

Column 9 Line 30 after "XbaI" insert --;--.

Column 9 Line 67 delete "and cut" (second occurrence).

Column 11 Line 20 "audioradiogram" should read --autoradiogram--.

Column 11 Line 48 "plaques For" should read --plaques. For--.

Column 12 Line 22 "then be" should read --then been--.

Column 12 Line 62 "Xba I" should read --XbaI--.

Column 12 Line 67 "0.2 sec;" should read --0.2 sec.;--.

Column 14 Line 1 "Hay A," should read --Hay, A.,--.

UNITED STATES PATENT AND TRADEMARK OFFICE
CERTIFICATE OF CORRECTION

PATENT NO. : 5,470,706
DATED : November 28, 1995
INVENTOR(S) : Jan Vijg and Jan A. Gossen It is certified that error appears in the above-indentified patent and that said Letters Patent is hereby corrected as shown below:

Column 14 Line 16 "Zeiger E et al." should read --Zeiger, E. et al.--.

Claim 6 Line 32 Column 15 after "further is" insert --selected as being--.

Claim 6 Lines 42-43 Column 15 "incapable selected as being" should read --selected as being incapable--.

Claim 8 Line 63 Column 15 "is capable" should read --is selected as being capable--.

Claim 11 Line 23 Column 16 "80, and" should read --80 and--.

Claim 16 Line 15 Column 17 "incapable selected as being" should read --selected as being incapable--.

Claim 16 Lines 21-22 Column 17 after "arrangement" insert --,--.

UNITED STATES PATENT AND TRADEMARK OFFICE
CERTIFICATE OF CORRECTION

PATENT NO. : 5,470,706
DATED : November 28, 1995
INVENTOR(S) : Jan Vijg and Jan A. Gossen It is certified that error appears in the above-indentified patent and that said Letters Patent is hereby corrected as shown below:

Claim 19 Lines 45-46 Column 17 "incapable of host selected as being" should read --selected as being incapable of host--.

Claim 20 Line 18 Column 18 "transgenie" should read --transgenic--.

Signed and Sealed this

Twenty-seventh Day of August, 1996

BRUCE LEHMAN

Attest:

Attesting Officer

Commissioner of Patents and Trademarks